(12) United States Patent
Young et al.

(10) Patent No.: US 11,020,490 B2
(45) Date of Patent: Jun. 1, 2021

(54) ANTIBODY-DRUG CONJUGATE WITH A TUBULYSIN ANALOG WARHEAD HAVING A STABILIZED ACETATE GROUP IN THE TUV SUBUNIT

(71) Applicant: BRISTOL-MYERS SQUIBB COMPANY, Princeton, NJ (US)

(72) Inventors: Ian S. Young, Redwood City, CA (US); Sha Lou, North Brunswick, NJ (US); Sanjeev Gangwar, Foster City, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 168 days.

(21) Appl. No.: 16/437,047

(22) Filed: Jun. 11, 2019

(65) Prior Publication Data

US 2019/0388553 A1 Dec. 26, 2019

Related U.S. Application Data

(60) Provisional application No. 62/688,737, filed on Jun. 22, 2018.

(51) Int. Cl.
*A61K 47/00* (2006.01)
*A61K 47/68* (2017.01)
*C07K 5/10* (2006.01)

(52) U.S. Cl.
CPC ............ *A61K 47/6811* (2017.08); *C07K 5/10* (2013.01)

(58) Field of Classification Search
CPC ....... A61K 47/6811; C07K 5/10; C07K 5/021
See application file for complete search history.

(56) References Cited

U.S. PATENT DOCUMENTS

| 8,268,970 | B2 | 9/2012 | Terrett |
| 8,394,922 | B2 | 3/2013 | Cheng et al. |
| 8,980,824 | B2 | 3/2015 | Cong |
| 2016/0130299 | A1 | 5/2016 | Perez |
| 2017/0326247 | A1 | 11/2017 | Cong |

OTHER PUBLICATIONS

Domling et al., Total Synthesis of Tubulysin U and V, 2006, 7235_7239, 45, Angewandte.
Khalil et al., Mechanism of Action of Tubulysin, an Antimitotic Peptide from Myxobacteria, 2006, 678_683, 7, Chembiochem.
Schrama et al., Antibody targeted drugs as cancer, 2006, 147-159, 5, Nature Rev Drug Disc, US.

*Primary Examiner* — James H Alstrum-Acevedo
*Assistant Examiner* — Mercy H Sabila
(74) *Attorney, Agent, or Firm* — Yuan Chao

(57) ABSTRACT

In antibody-drug conjugates having tubulysin analog as the warhead, according to formula (III)

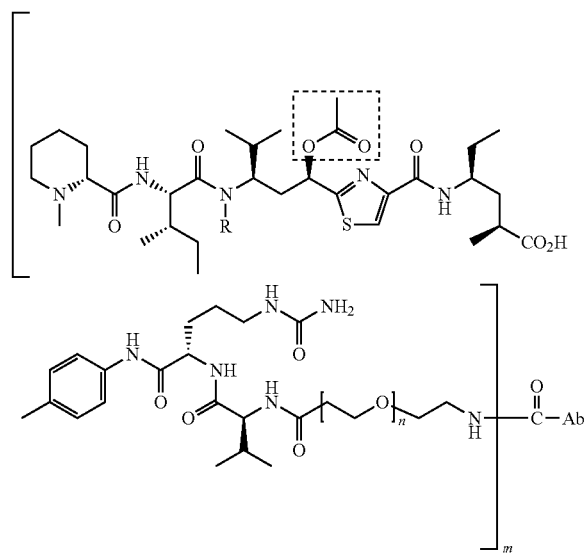

the acetate group in the Tuv subunit (dotted box) demonstrates improved stability against hydrolytic cleavage.

4 Claims, 2 Drawing Sheets

ANTIBODY-DRUG CONJUGATE WITH A TUBULYSIN ANALOG WARHEAD HAVING A STABILIZED ACETATE GROUP IN THE TUV SUBUNIT

CROSS-REFERENCE TO RELATED APPLICATIONS

This application claims the benefit under 35 U.S.C. § 119(e) of U.S. Provisional Application Ser. No. 62/688,737, filed Jun. 22, 2018; the disclosure of which is incorporated herein by reference.

BACKGROUND OF THE INVENTION

This invention relates to antibody-drug conjugates of tubulysin analogs having enhanced stability, tubulysin analog-linker compounds for making such antibody-drug conjugates, methods for preparing such antibody-drug conjugates and for their use.

A type of anticancer agent that is generating strong interest is an antibody-drug conjugate (ADC, also referred to as an immunoconjugate). In an ADC, a therapeutic agent, also referred to as the drug, cytotoxin, payload, or warhead, is covalently linked to an antibody whose antigen is expressed by a cancer cell (tumor associated antigen). The moiety covalently linking the antibody and the drug is referred to as the linker. In the case where each antibody has one drug attached to it, the structure of an ADC can be generally represented as:

[Antibody]-[Linker]-[Drug]

The antibody, by binding to the antigen, delivers the ADC to the cancer site. There, cleavage of the linker or degradation of the antibody leads to the release of the therapeutic agent. Conversely, while the ADC is circulating in the blood system, the therapeutic agent is held inactive because of its covalent linkage to the antibody. Thus, the therapeutic agent used in an ADC can be much more potent (i.e., cytotoxic) than ordinary chemotherapy agents because of its localized release. For a review on ADCs, see Schrama et al. 2006. (The full bibliographic citation for this and other documents cited herein by first author or inventor and year are listed at the end of this specification.)

One class of compounds that has been proposed as the drug in an ADC are tubulysin analogs. The tubulysins are anti-mitotic naturally occurring cytotoxins, first isolated from myxobacteria cultures. During mitosis, a cell's microtubules reorganize to form the mitotic spindle, a process requiring the rapid assembly and disassembly of microtubules from their constituent proteins α- and β-tubulin. The cytotoxicity of the tubulysins derives from their ability to prevent the assembly of the tubulins into microtubules, causing the affected cells to accumulate in the $G_2/M$ phase and undergo apoptosis (Khalil et al. 2006).

The tubulysins have a tetrapeptidyl scaffold consisting of one proteinogenic and three non-proteinogenic amino acid subunits as shown in formula (A): N-methylpipecolinic acid (Mep), isoleucine (Ile), tubuvaline (Tuv), and either tubuphenylalanine (Tup, R' equals H) or tubutyrosine (Tut, R' equals OH). Structural variations among the tubulysins (named A, B, etc.) center around residues R', R" and R'" of formula (A), as shown in Table I.

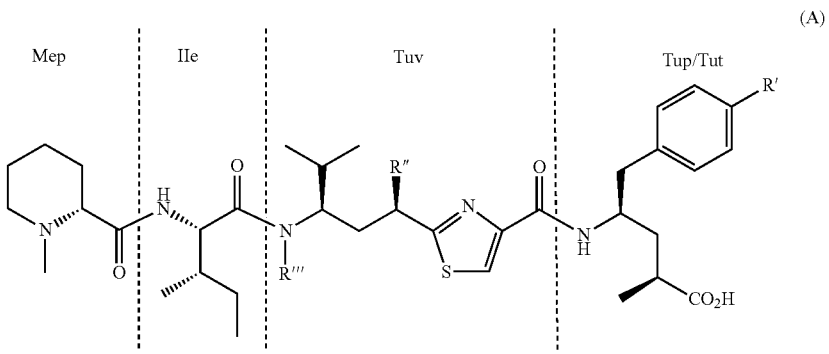

(A)

TABLE I

| Naturally Occurring Tubulysins | | | |
|---|---|---|---|
| Tubulysin | R' | R" | R'" |
| A | OH | OC(=O)Me | $CH_2OC$(=O)i-Bu |
| B | OH | OC(=O)Me | $CH_2OC$(=O)n-Pr |
| C | OH | OC(=O)Me | $CH_2OC$(=O)Et |
| D | H | OC(=O)Me | $CH_2OC$(=O)i-Bu |
| E | H | OC(=O)Me | $CH_2OC$(=O)n-Pr |
| F | H | OC(=O)Me | $CH_2OC$(=O)Et |
| G | OH | OC(=O)Me | $CH_2OC$(=O)CH=$CH_2$ |
| H | H | OC(=O)Me | $CH_2OC$(=O)Me |
| I | OH | OC(=O)Me | $CH_2OC$(=O)Me |
| U | H | OC(=O)Me | H |
| V | H | OH | H |
| Y | OH | OC(=O)Me | H |
| Z | OH | OH | H |
| Pretubulysin | H | H | Me |

Cheng et al. 2013 and Perez et al. 2016 disclose ADCs of tubulysin analogs, in particular analogs having at the R' position of formula (A) above an amino ($NH_2$) group, which can serve as an attachment site for the linker.

The acetate group in the Tuv subunit appears to be essential for biological activity. Its removal (deacetylation), resulting in compounds in which R" in formula (A) is hydroxyl, reportedly leads to loss of biological activity (Domling et al. 2006). In a study of tubulysins U and V, which differ in the former being acetylated and the latter being deacetylated, tubulysin V was reported to be less potent by about 200× to 600×, depending on the assay (Balasubramanian et al. 2009). Because an acetate group can be susceptible to hydrolysis, deacetylation at the R" position is a concern in the development of tubulysin analogs as the drug in an ADC. If deacetylation occurs, cleavage of the linker would lead to release of an inactive drug.

Cong et al. 2015 have proposed addressing this issue by replacing the naturally occurring acetate group in the Tuv subunit with a more hydrolytically resistant moiety such as a carbamate:

Cong et al. 2017 discloses that positioning a methyleneamino ($CH_2NH_2$) group (dotted box) adjacent to the maleimide group in a tubulysin-linker compound such as shown in formula (B) below results in an ADC having improved stability of the acetate group.

BRIEF SUMMARY OF THE INVENTION

We have discovered that a tubulysin of formula (I), when coupled to a particular type of linker group, leads to an ADC having unexpectedly improved stability of the Tuv acetate group against deacetylation.

(where R is $C_1$-$C_4$ alkyl).

In one aspect, this disclosure provides a compound having a structure according to formula (II)

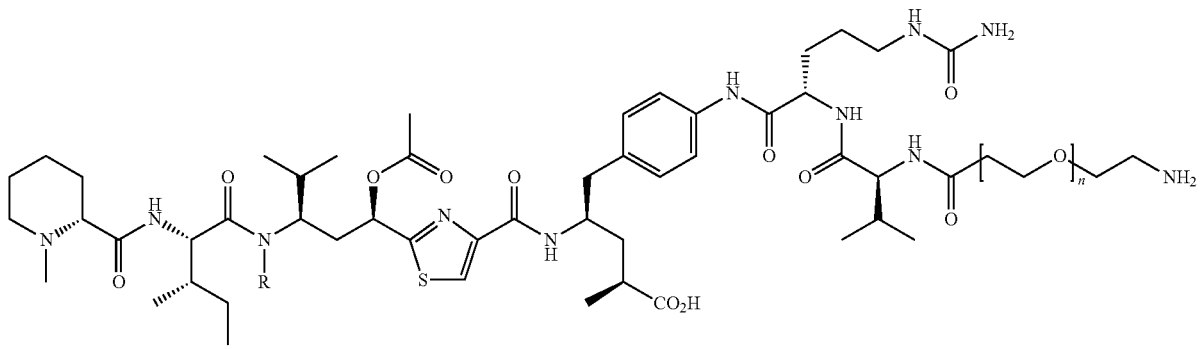

(II)

where R is $C_1$-$C_4$ alkyl, preferably Me or n-Pr; and the subscript n is 2, 3, 4, 5, 6, 7, or 8; preferably 2, 4, or 8; and more preferably 4.

In the more preferred instance where R is n-Pr and n is 4, the corresponding structure is provided by formula (II'):

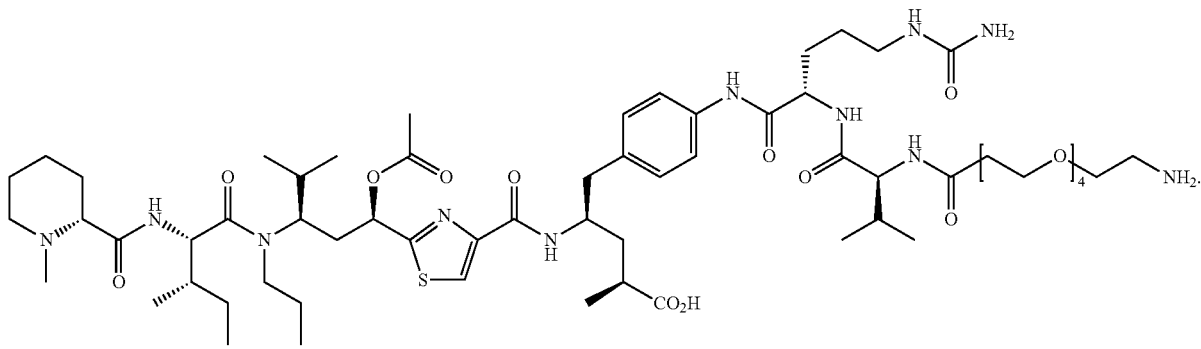

(II')

Compounds of formula (II) can be conjugated to an antibody to prepare an antibody-drug conjugate having a structure according to formula (III):

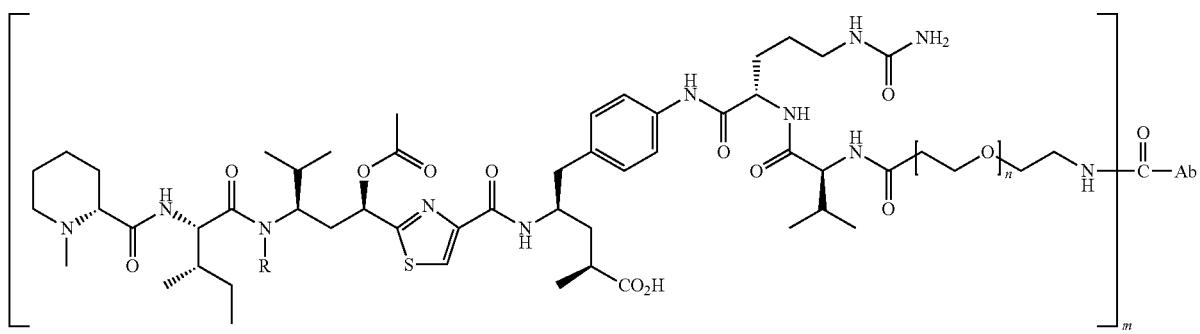

(III)

where R is $C_1$-$C_4$ alkyl, preferably Me or n-Pr; Ab is an antibody; n is 2, 3, 4, 5, 6, 7, or 8; preferably 2, 4, or 8; and more preferably 4; and m is 1, 2, 3, 4, 5, or 6; preferably 1, 2, 3, or 4; and more preferably 2 or 4.

In a preferred embodiment, the antibody-drug conjugate is according formula (III')

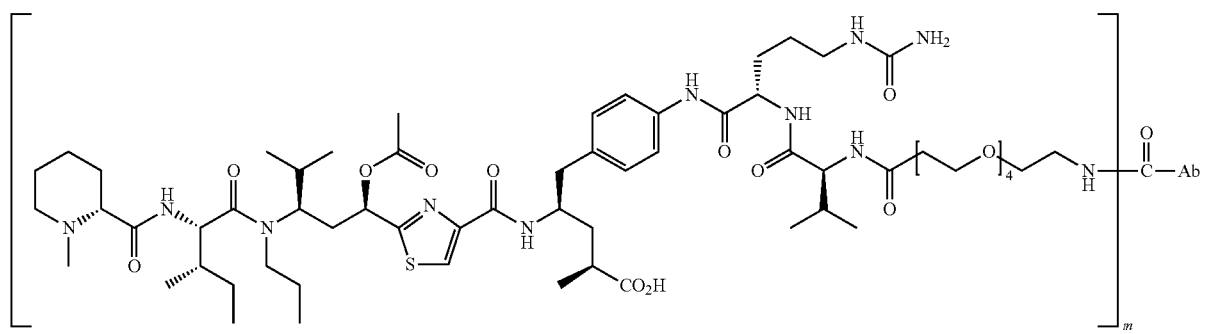

(III')

where Ab and m are as defined above, with m preferably being 1, 2, 3, or 4.

BRIEF DESCRIPTION OF THE DRAWING(S)

DETAILED DESCRIPTION OF THE INVENTION

Definitions

Figure 1:
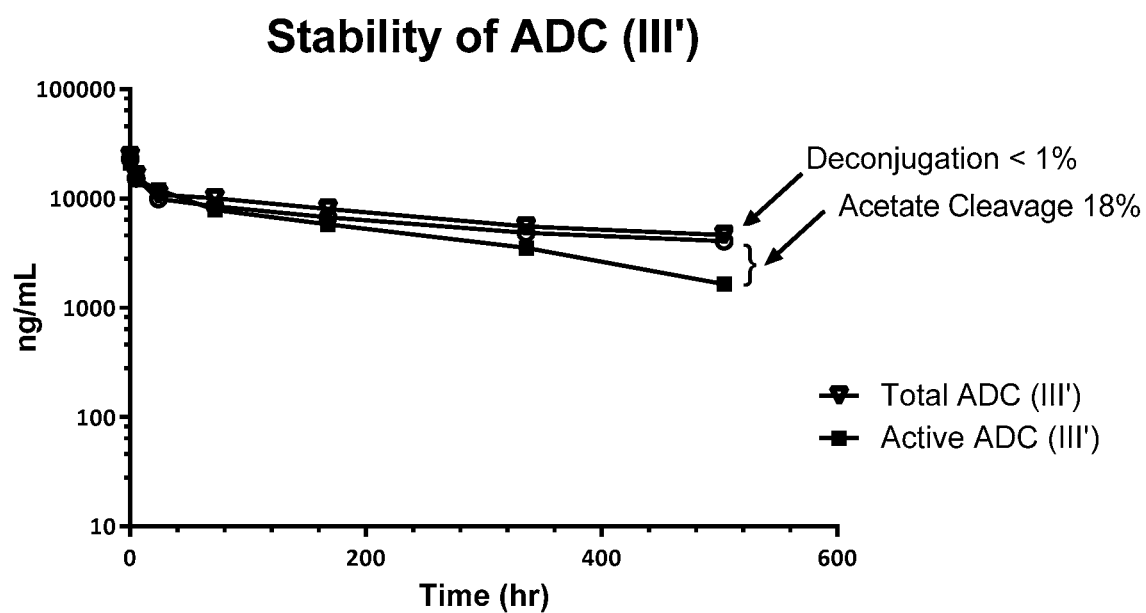
FIG. 1 shows the extent of hydrolysis of the Tuv acetate group over three weeks in an ADC made from a tubulysin analog-linker compound according to formula (II).

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$M or less, more preferably $1\times10^{-8}$M or less, more preferably $6\times10^{-9}$ M or less, more preferably $3\times10^{-9}$ M or less, even more preferably $2\times10^{-9}$M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$, and $V_H$, are encoded by separate genes, they can be joined, using recombinant methods, by a synthetic linker that enables them to be made as a single protein chain in which the $V_L$, and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germ-line immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human anti-body" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.+

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocyclo-aliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)

NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are C$_1$-C$_4$ alkyl, cyano, nitro, halo, and C$_1$-C$_4$alkoxy.

Where a range is stated, as in "C$_1$-C$_5$ alkyl" or "5 to 10%," such range includes the end points of the range, as in C$_1$ and C$_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C$_1$-C$_5$ alkyl, C$_2$-C$_5$ alkenyl or C$_2$-C$_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ( ~~~ ) transverse to a bond or an asterisk (*) at the end of the bond denotes a covalent attachment site. For instance, a statement that R is

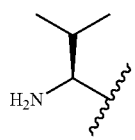 or that R is  in the formula

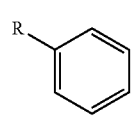 means 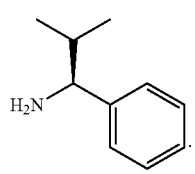.

In the formulae of this specification, a bond traversing an aromatic ring between two carbons thereof means that the group attached to the bond may be located at any of the available positions of the aromatic ring. By way of illustration, the formula

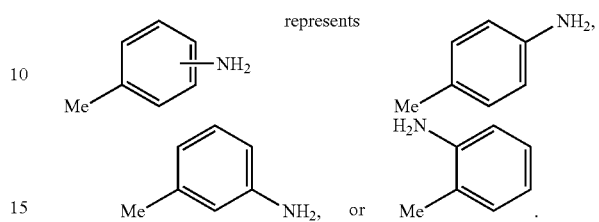

Conjugates

A common conjugation technique uses the enzyme transglutaminase, per Jeger et al., *Angew. Chem. Int. Ed.* 2010, 49, 9995. When acting on polypeptides, transglutaminase forms an amide bond between the side chain carboxamide of a glutamine (the amine acceptor) and the ε-amino group of a lysine (the amine donor). If the glutamine and lysine are on separate polypeptide chains, the two chains become linked to each other. Specificity-wise, transglutaminase is selective regarding the amine acceptor, requiring that it be a glutamine located in a flexible part of a polypeptide loop and be flanked by particular amino acids. Conversely, it is permissive regarding the amine donor. While the natural substrate is the lysine ε-amino group, it readily accepts an amino group from a non-protein source, such as a 5-amino-n-pentyl group. See Fontana et al., *Adv. Drug Deliv. Rev.* 2008, 60, 13.

A commonly used transglutaminase is bacterial transglutaminase from *Streptomyces mobaraensis*. The acronym TGase is often used for transglutaminase, while the acronym BTG is used for bacterial transglutaminase. However, since by far the most commonly used transglutaminase is of bacterial origin (especially from *S. mobaraensis*), the two acronyms are used somewhat interchangeably. Transglutaminase from other bacteria, having somewhat different substrate specificities, can be utilized, such as transglutaminase from *Streptoverticillium ladakanum* (Hu et al., US 2009/0318349 A1 (2009), US 2010/0099610 A1 (2010), and US 2010/0087371 A1 (2010)).

In a typical conjugation reaction, the glutamine residue is located on the antibody, while the alkyleneamino group is located on the linker-drug moiety, as shown below:

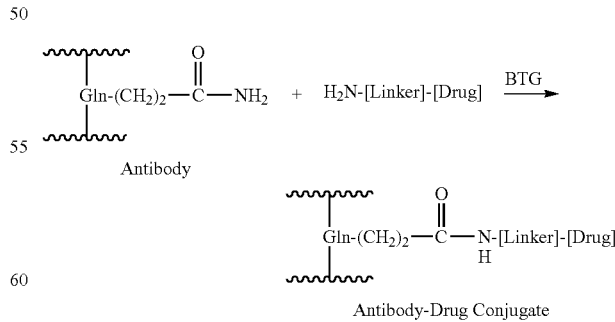

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297; numbering per EU index as set forth in Kabat et al., "Sequences of proteins of immunological interest," 5th ed., Pub. No. 91-3242, U.S. Dept. Health & Human Services, NIH, Bethesda, Md., 1991; hereinafter "Kabat") of the heavy chain—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A site-specific mutation (replacing asparagine 297 with an alanine) in the constant region, to eliminate the N297 glycosylation site. Further, it has been shown that an N297Q substitution (replacing asparagine 297 with a glutamine) not only eliminates glycosylation, but also introduces a second glutamine (at position 297) that too is an amine acceptor. Thus, in one embodiment, the antibody is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

An antibody can also be rendered susceptible to BTG-mediated conjugation by introducing into it a glutamine containing peptide, or "tag," as taught, for example, in Pons et al., US 2013/0230543 A1 (2013) and Rao-Naik et al., WO 2016/144608 A1.

In a complementary approach, the substrate specificity of BTG can be altered by varying its amino acid sequence, such that it becomes capable of reacting with glutamine 295 in an umodified antibody, as taught in Rao-Naik et al., PCT Application PCT/US2016/054585, filed 30 Sep. 2016.

A compounds of formula (II) have an alkylene amino group (dotted box), which can sever as an amine donor.

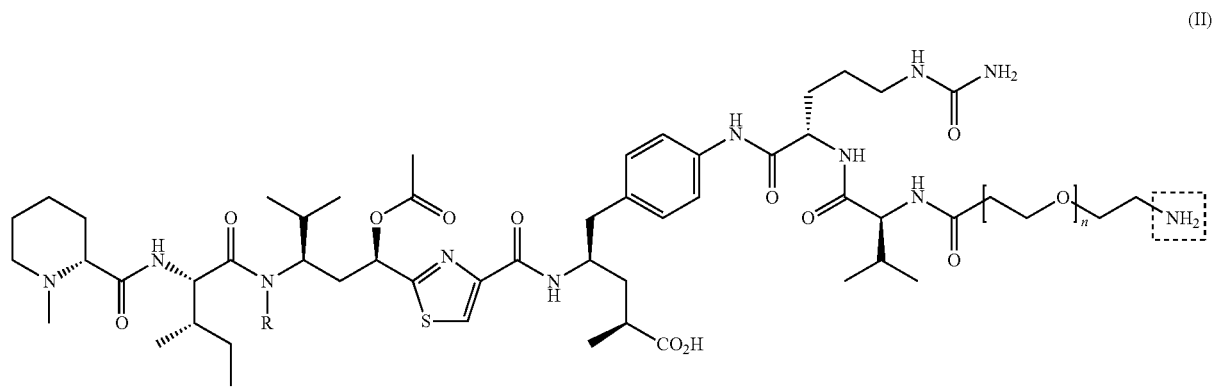

(II)

BTG-mediated conjugation conjugation of compounds (II) with an antibody—for example, one having an N297A or N297Q substitution or which one that has been enzymatically deglycosylated—provides a conjugate of formula (III)

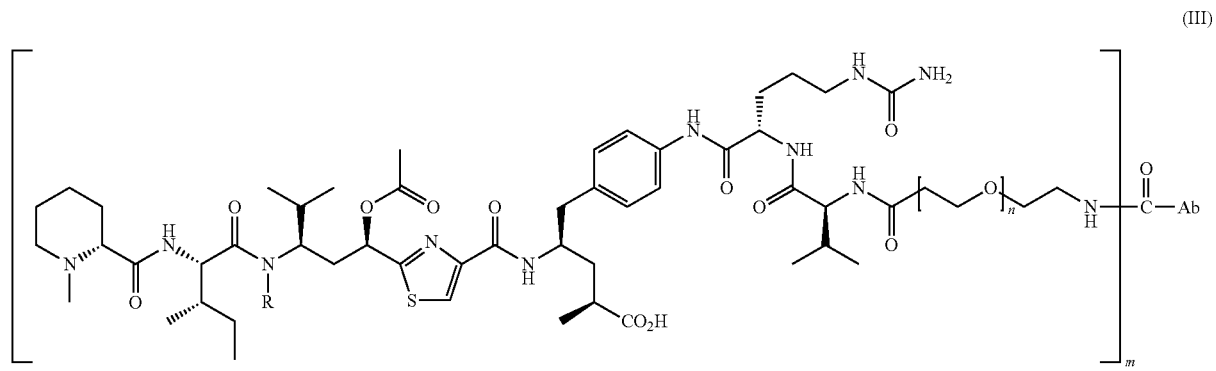

(III)

where R is $C_1$-$C_4$ alkyl, preferably Me or n-Pr; Ab is an antibody; n is 2, 3, 4, 5, 6, 7, or 8; preferably 2, 4, or 8; and more preferably 4; and m is 1, 2, 3, 4, 5, or 6; preferably 1, 2, 3, or 4; and more preferably 2 or 4.

The theoretical value of m will vary according to the number of BTG-reactive glutamines in the antibody. For an antibody having an N297A substitution, it will be 2. But for an antibody having an N297Q substitution, the theoretical value of m will be 4, as discussed above. The actual value of m may be less than the theoretical value, if the conjugation reaction is not 100% efficient. There could be conjugate molecules where m is 1 or 2 in the instance of an N297A antibody and where m could be 1, 2, 3 or 4 in the instance of an N297Q antibody.

Those skilled in the art will appreciate that, while m is an integer for a given conjugate molecule, a preparation of the conjugate may analyze for a non-integer ratio of drug-linkers attached to an antibody, reflecting a statistical average of the conjugate molecules in the preparation. This ratio is referred to as the substitution ratio (SR) or, synonymously, the drug-antibody ratio (DAR).

In a preferred embodiment, n is 4, corresponding to a conjugate having structure according to formula (III'):

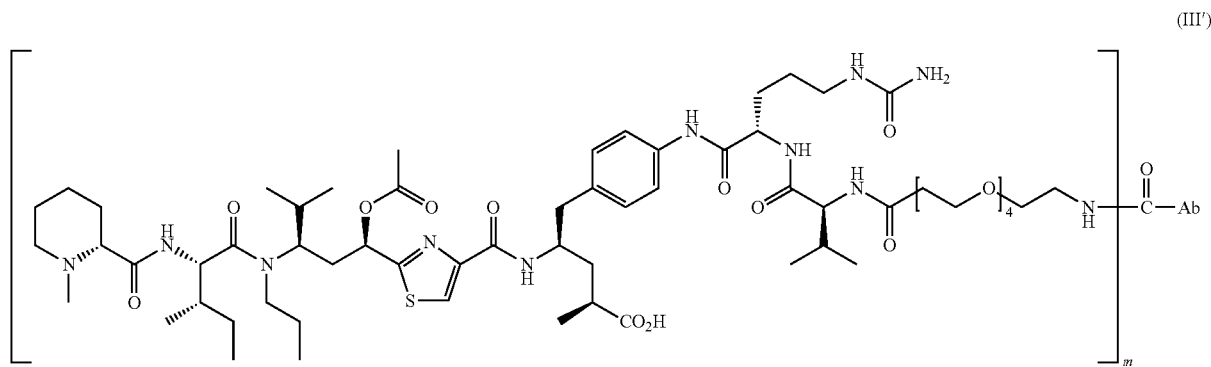

(III')

where Ab and m are as previously defined, with m preferably being 1, 2, 3 or 4.

We have discovered that, unexpectedly, tubulysin analog-linker compounds of formula (II) produce conjugates in which hydrolysis of the acetate group in the Tuv subunit is significantly reduced.

This enhanced stability is demonstrated via comparative data against an ADC prepared from tubulysin analog-linker compound (C), which has the same tubulysin analog for a warhead but a different linker (Cheng et al. 2013):

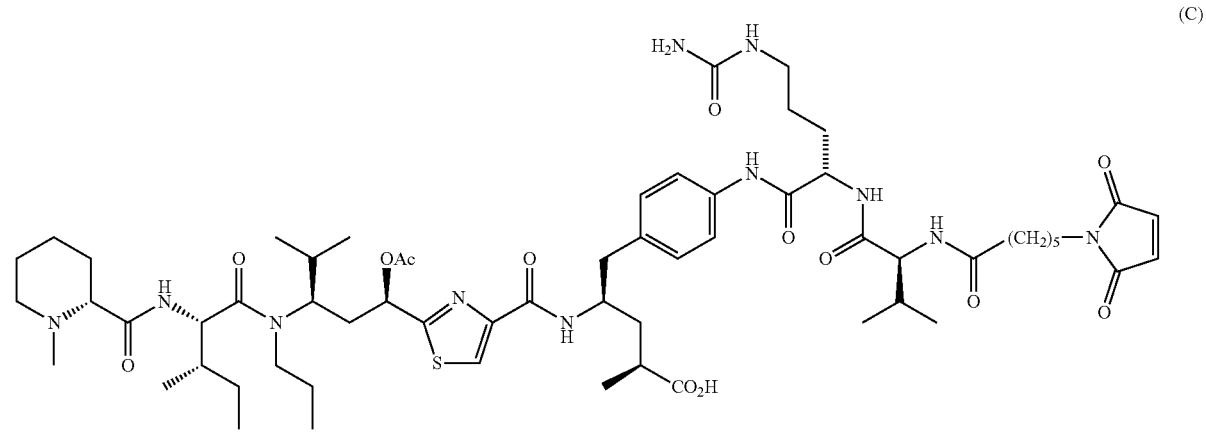

(C)

The linker in compound (C) differs from that of compound (II) in that it lack poly(ethylene glycol) ("PEG") groups and the terminal maleimide group is designed for conjugation via 2-iminothiolane ("2-IT") chemistry, as opposed to BTG-mediated transamidation (Cheng et al. 2013). The structure of the resulting ADC is represented by formula (C'):

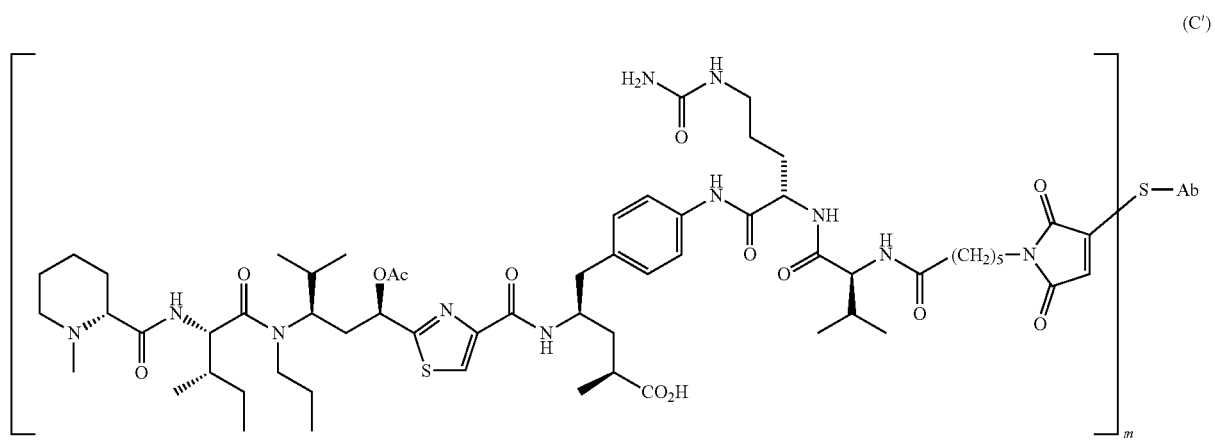

(C')

Figure 2:
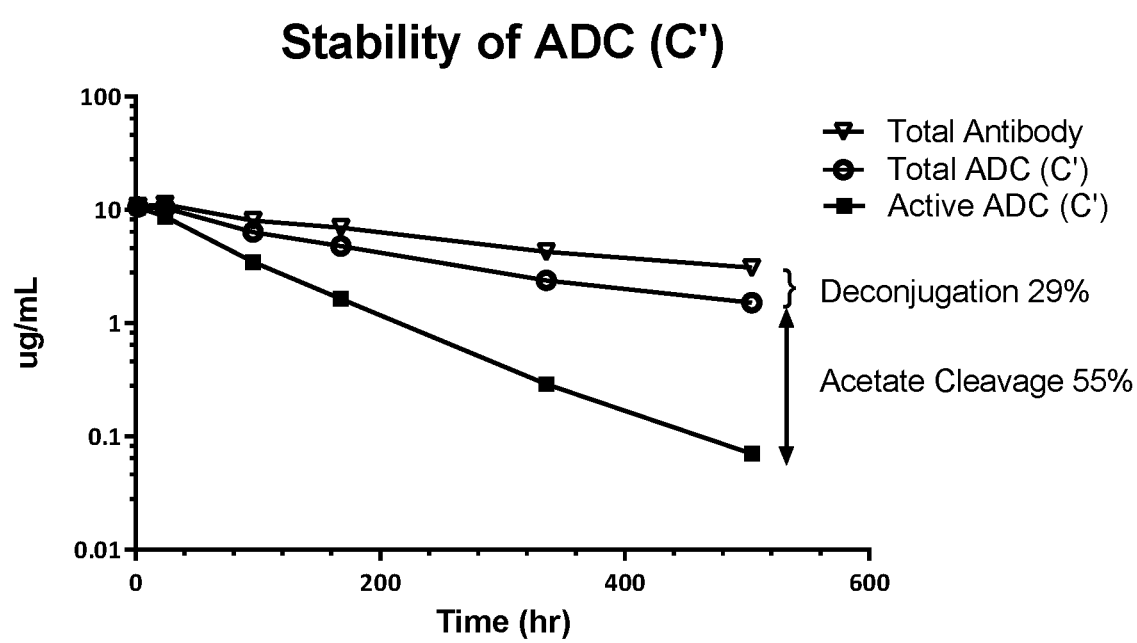
FIG. 2 shows the extent of hydrolysis of the Tuv acetate group over three weeks in an ADC made from a comparative tubulysin analog linker, which has identical tubulysin analog as in formula (II) but a different linker.

FIG. 1 shows the stability of the Tuv acetate group in the ADC (III') over the course of three weeks, whereas FIG. 2 shows the stability of the Tuv acetate group in ADC (C'), also over the course of three weeks. (The antibody in ADC was a mesothelin antibody (Terrett et al. 2012)). The total amount of ADC present was detected using an antibody (designated 8F3) that binds to the ADC regardless of the hydrolytic state of the Tuv acetate. The amount of active ADC was detected using an antibody (designated 14A2) that binds to the ADC only if the Tuv acetate is un-hydrolyzed.

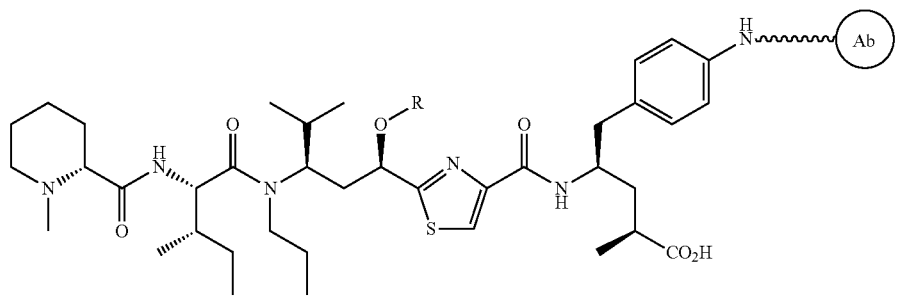

8F3: recognizes either X equals C(=O)CH$_3$ or H
14A2: recognizes R equals C(=O)CH$_3$ only The results from the two figures are compared side-by-side in Table I.

|       | (Active ADC)/(Total ADC) | |
| ADC   | 1 week | 3 weeks |
| --- | --- | --- |
| (C')  | 55%  | 32% |
| (III')| 98%  | 82% |

The practice of this invention can be further understood by reference to the following examples, which are provided by way of illustration and not of limitation.

Example 1—Compound (II')

This example relates to the synthesis of compound (II').

(II')

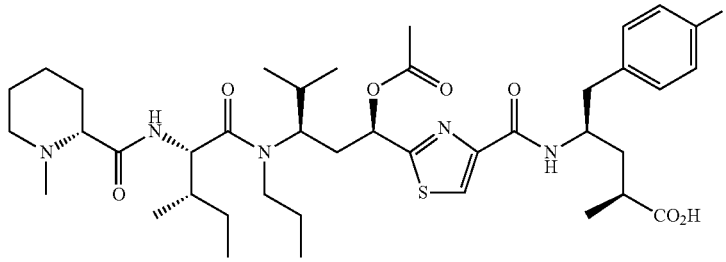

Three synthetic precursors D, E, and F were used to prepare compound (II'):

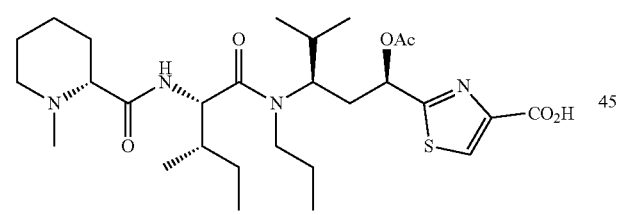

D

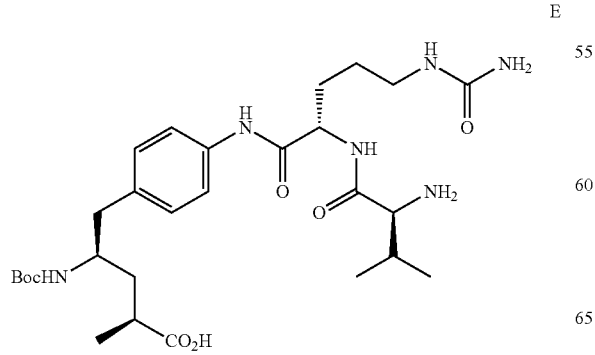

E

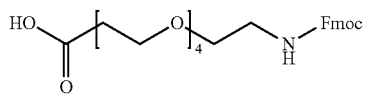

F

The preparation of compound D is disclosed in Cheng et al. 2013 (compound 108, FIG. 19). The preparation of compound E is disclosed in Cong et al. 2015 (compound 21, FIG. 2b). Compound F was prepared from tert-butyl 1-amino-3,6,9,12-tetraoxapentadecan-15-oate (CAS Reg. No. 581065-95-4) by treatment with Fmoc-Cl to attach the Fmoc protecting group, followed by treatment with trifluoroacetic acid to cleave the t-butyl ester.

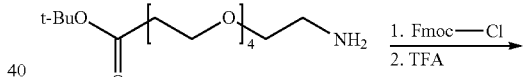

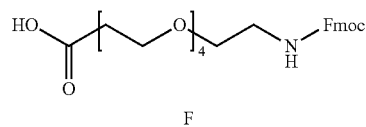

F

The coupling of compounds E and F using HATU, followed by removal of the Boc protecting group with trifluoroacetic acid afforded compound G:

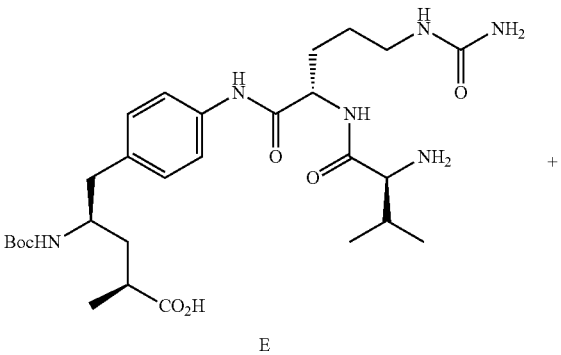

E

-continued

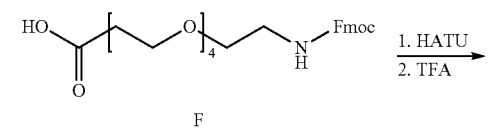

F

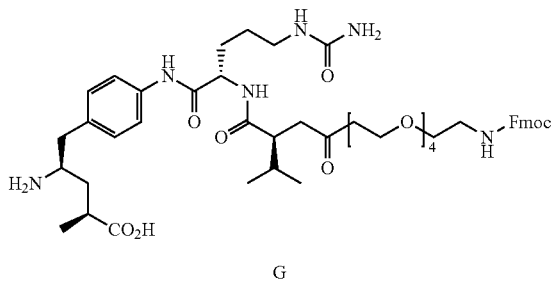

G

Lastly, HATU-mediated coupling of compounds D and G, followed by removal of the Fmoc group with diethylamine yielded compound (II').

Example 2—Transglutaminase-Mediated Conjugation

The following procedure can be used for transglutaminase mediated conjugation. The antibody can be one that has a transglutaminase-reactive glutamine, for example one with an N297A or N297Q substitution. Conjugation is carried out by recombinant bacterial transglutaminase with a molar ratio of antibody:enzyme of 5:1. The conjugation is carried out using standard protocols in 50 mM Tris buffer, pH 8.0, incubated overnight at 37° C. The resulting conjugate is purified on a Protein A column, pre-equilibrated with 50 mM Tris, pH 8.0. The conjugate is eluted with 0.1 M sodium citrate buffer, pH 3.5. The eluted fractions are neutralized with 1M Tris pH 9.0. The conjugate can be formulated in 20 mg/mL Sorbitol, 10 mg/mL Glycine, pH 5.0.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Cheng et al., U.S. Pat. No. 8,394,922 B2 (2013).
Cong et al., U.S. Pat. No. 8,980,824 B2 (2015).
Cong et al., US 2017/0326247 A1 (2017).
Domling et al., Ang. Chem. Int. Ed. 2006, 45, 7235-7239.
Khalil et al., Chem Bio Chem 2006, 7, 678.
Perez et al., US 2016/0130299 A1 (2016).
Schrama et al., Nature Rev. Drug Disc. 2006, 5, 147-159.
Terrett et al., U.S. Pat. No. 8,268,970 B2 (2012).

What is claimed is:

1. A compound having a structure according to formula (II)

(II)

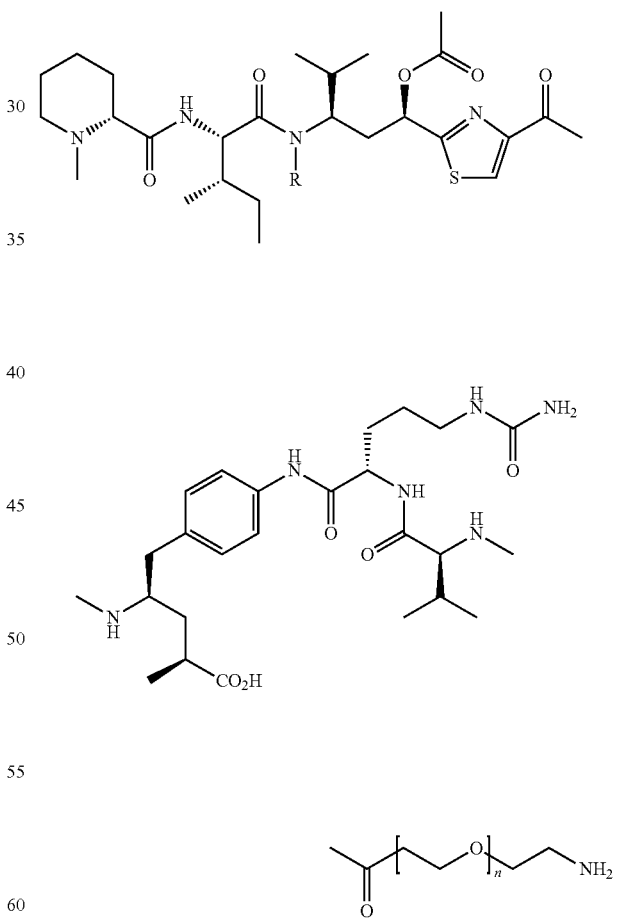

where R is $C_1$-$C_4$ alkyl and the subscript n is 2, 3, 4, 5, 6, 7, or 8.

2. A compound according to claim 1, having a structure according to formula (II'):
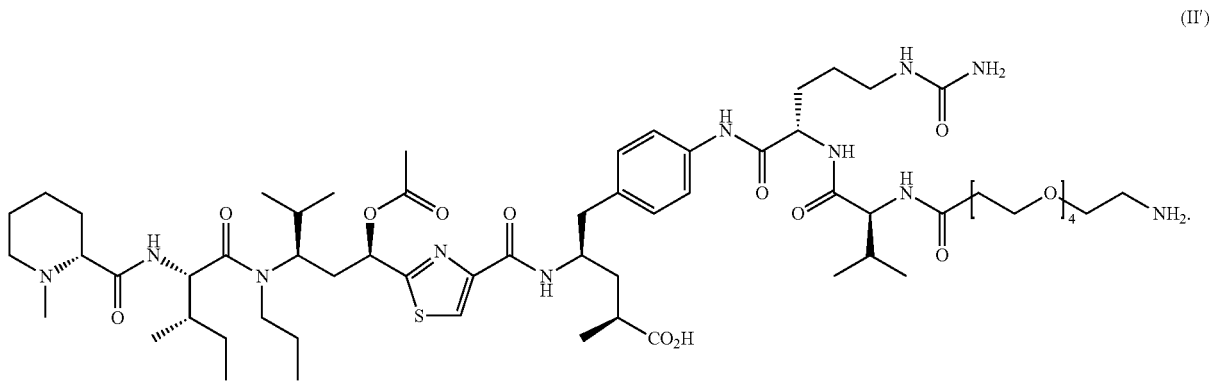
(II')
3. An antibody-drug conjugate having a structure according to formula (III):
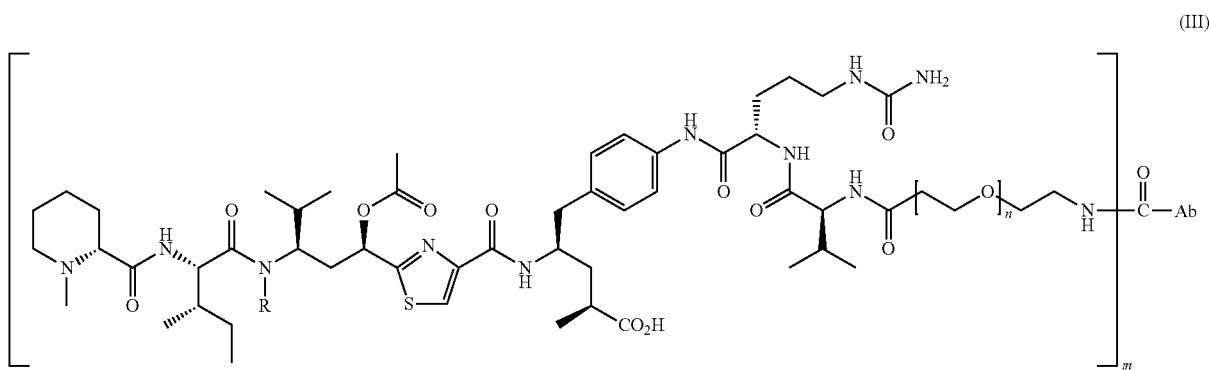
(III)
where R is $C_1$-$C_4$ alkyl; Ab is an antibody; n is 2, 3, 4, 5, 6, 7, or 8; and m is 1, 2, 3, 4, 5, or 6.
4. An antibody-drug conjugate according to claim 3, having a structure according to formula (III'):
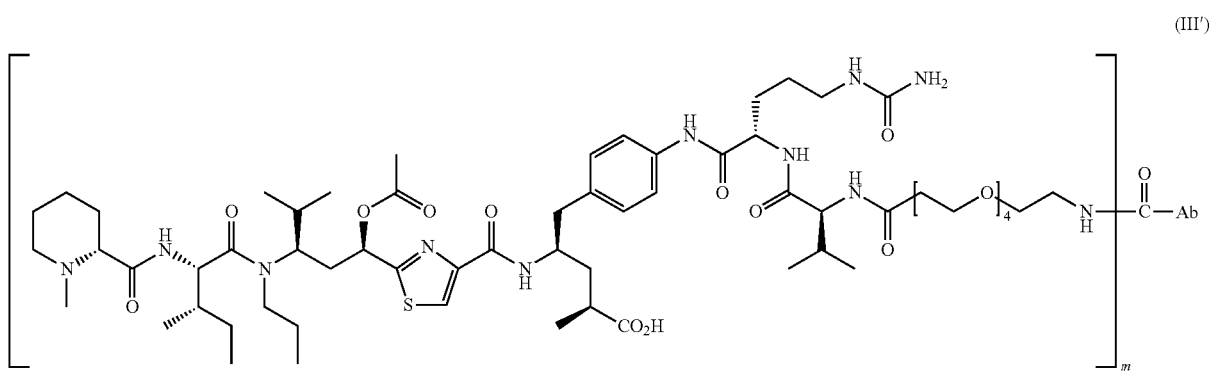
(III')
where m is 1, 2, 3, or 4.
* * * * *